United States Patent [19]

Sheth et al.

[11] Patent Number: 5,428,011
[45] Date of Patent: Jun. 27, 1995

[54] PHARMACEUTICAL PREPARATIONS FOR INHIBITING TUMOURS ASSOCIATED WITH PROSTATE ADENOCARCINOMA

[75] Inventors: Anil R. Sheth; Seema Garde, both of Bombay, India; Chandra J. Panchal, Lambeth, Canada

[73] Assignee: Procyon Biopharma, Inc., Canada

[21] Appl. No.: 899,535

[22] Filed: Jun. 16, 1992

[51] Int. Cl.6 .................. A61K 38/00; C07K 5/00; C07K 7/00; C07K 14/00
[52] U.S. Cl. .................................. 514/12; 530/300; 530/324
[58] Field of Search ................. 530/324, 300; 514/12

[56] References Cited

U.S. PATENT DOCUMENTS 4,764,502  8/1988  diZerega ........................ 514/2
5,102,807  4/1992  Burger et al. .................. 436/518

OTHER PUBLICATIONS

Prostate as an Endrocrine Gland, Chapter 9, pp. 131–178; W. E. Farnsworth & R. G. Ablin, Publisher; CRC Press, Fla., 1990.

Primary Examiner—Jill Warden
Assistant Examiner—A. M. Davenport
Attorney, Agent, or Firm—Hill & Schumacher

[57] ABSTRACT

The present invention provides pharmaceutical preparations for inhibiting in-vitro and in-vivo cancerous prostate, gastrointestinal and breast tumors. In one embodiment the pharmaceutical preparation includes human seminal prostatic inhibin which may be administered in an appropriate dosage form, dosage quantity and dosage regimen to a patient suffering from prostate cancer. In another embodiment the pharmaceutical preparation includes a mixture of human seminal prostatic inhibin and a anticancer drug which may be administered in an appropriate dosage form, dosage quantity and dosage regimen to a patient suffering from, for example gastrointestinal cancer. The anticancer drug of the latter mixture may be one selected from the group of drugs including mitomycin, idalubicin, cisplatin, 5-fluorouracil, methotrexate, adriamycin and daunomycin.

10 Claims, 20 Drawing Sheets

```
NH2-Ser Cys Tyr Phe Ile Pro Asn Glu Gly Val
     1               5                    10

Pro Gly Asp Ser Thr Arg Lys Cys Met Asp
                        15                  20

Leu Lys Gly Asn Lys His Pro Ile Asn Ser
                        25                  30

Glu Trp Gln Thr Asp Asn Cys Glu Thr Cys
                        35                  40

Thr Cys Tyr Glu Thr Glu Ile Ser Cys Cys
                        45                  50

Thr Leu Val Ser Thr Pro Val Gly Tyr Asp
                        55                  60

Lys Asp Asn Cys Gln Arg Ile Phe Lys Lys
                        65                  70

Glu Asp Cys Lys Tyr Ile Val Val Glu Lys
                        75                  80

Lys Asp Pro Lys Lys Thr Cys Ser Val Ser
                        85                  90

Glu Trp Ile Ile-COOH
              94
```

```
NH2-Ser  Cys  Tyr  Phe  Ile  Pro  Asn  Glu  Gly  Val
  1                 5                        10

Pro  Gly  Asp  Ser  Thr  Arg  Lys  Cys  Met  Asp
                        15                       20

Leu  Lys  Gly  Asn  Lys  His  Pro  Ile  Asn  Ser
                        25                       30

Glu  Trp  Gln  Thr  Asp  Asn  Cys  Glu  Thr  Cys
                        35                       40

Thr  Cys  Tyr  Glu  Thr  Glu  Ile  Ser  Cys  Cys
                        45                       50

Thr  Leu  Val  Ser  Thr  Pro  Val  Gly  Tyr  Asp
                        55                       60

Lys  Asp  Asn  Cys  Gln  Arg  Ile  Phe  Lys  Lys
                        65                       70

Glu  Asp  Cys  Lys  Tyr  Ile  Val  Val  Glu  Lys
                        75                       80

Lys  Asp  Pro  Lys  Lys  Thr  Cys  Ser  Val  Ser
                        85                       90

Glu  Trp  Ile  Ile-COOH
                  94
```

FIGURE 1

Effect of FSH on Prostate Cancer Cell Growth In Vitro and Its Inhibition by HSPI

```
NH2-Ser  Cys  Tyr  Phe  Ile  Pro  Asn  Glu  Gly  Val
  1                    5                        10

Pro  Gly  Asp  Ser  Thr  Arg  Lys  Cys  Met  Asp
                        15                       20

Leu  Lys  Gly  Asn  Lys  His  Pro  Ile  Asn  Ser
                        25                       30

Glu  Trp  Gln  Thr  Asp  Asn  Cys  Glu  Thr  Cys
                        35                       40

Thr  Cys  Tyr  Glu  Thr  Glu  Ile  Ser  Cys  Cys
                        45                       50

Thr  Leu  Val  Ser  Thr  Pro  Val  Gly  Tyr  Asp
                        55                       60

Lys  Asp  Asn  Cys  Gln  Arg  Ile  Phe  Lys  Lys
                        65                       70

Glu  Asp  Cys  Lys  Tyr  Ile  Val  Val  Glu  Lys
                        75                       80

Lys  Asp  Pro  Lys  Tyr  Thr  Cys  Ser  Val  Ser
                        85                       90

Glu  Trp  Gly  Ile–COOH
                   94
```

```
                                                        ┌─R-17
       ┌─────────────────────────────────────────────────────────┐
NH2────│Ser   Cys   Tyr   Phe   Ile   Pro   Asn   Glu   Gly   Val│
       │ 1                      5                             10 │
       │                                           ┌─────────────┤
       │Pro   Gly   Asp   Ser   Thr   Arg   Lys   │Cys   Met   Asp
       │                        15                │            20
       └──────────────────────────────────────────┘
       Leu   Lys   Gly   Asn   Lys   His   Pro   Ile   Asn   Ser
                               25                             30

Glu   Trp   Gln   Thr   Asp   Asn   Cys   Glu   Thr   Cys
                               35                             40

Thr   Cys   Tyr   Glu   Thr   Ile   Ser   Cys   Cys
                               45                             50

Thr   Leu   Val   Ser   Thr   Pro   Val   Gly   Tyr   Asp
                               55                             60

Lys   Asp   Asn   Cys   Gln   Arg  ┌Ile   Phe   Lys   Lys
                               65         │                   70
       ┌──────────────────────────────────┘
       │Glu   Asp   Cys   Lys   Tyr   Ile   Val   Val   Glu   Lys
       │                        75                             80
       │
       │Lys   Asp   Pro   Lys   Lys   Thr   Cys   Ser   Val   Ser
       │                        85                             90
       │
       │Glu   Trp   Gly   Ile├──COOH                        ╲
       │                   94                                ╲
       └────────────────────┘                                 R-28
```

FIGURE 12

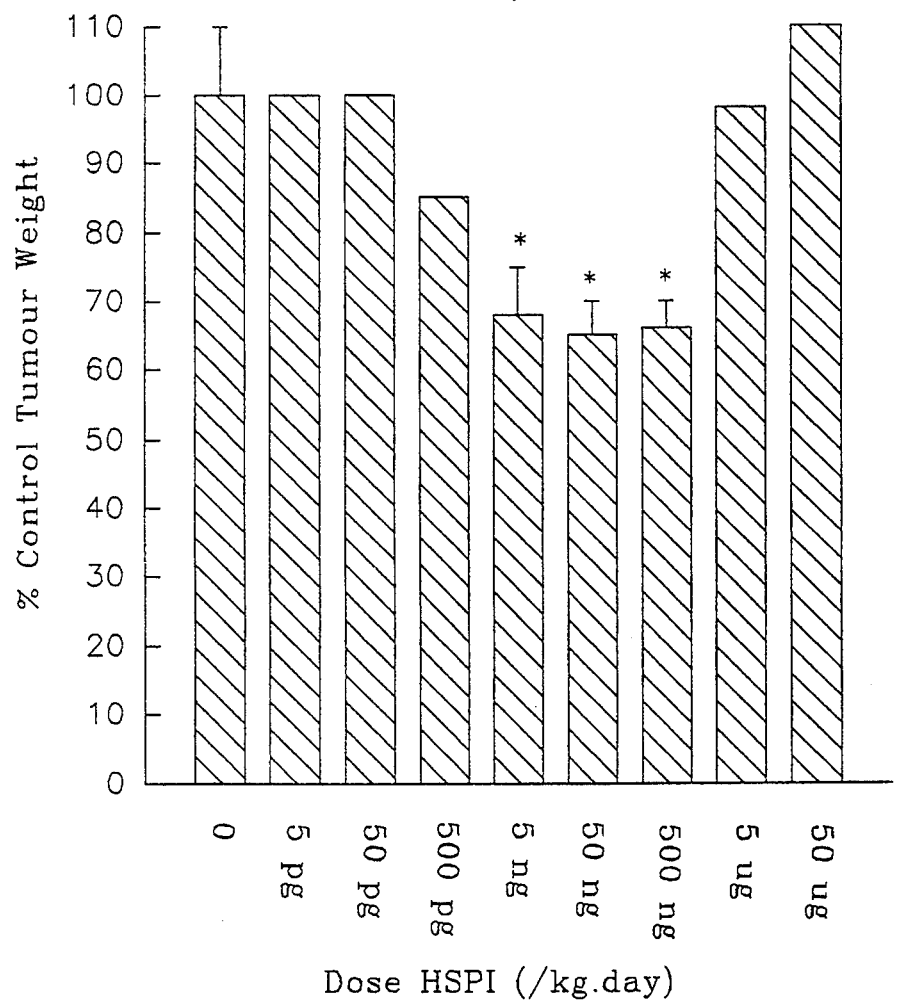

Cytotoxic Effect of HSPI With/Without Donomycin on Human Gastric Cancer Cell Line Cytotoxic Effect of HSPI With/Without Adriamycin on Human Gastric Cancer Cell Line Cytotoxic Effect of HSPI With/Without Cisplatin on Human Gastric Cancer Cell Line Cytotoxic Effect of HSPI With/Without 5-Fluorouracil (5-FU) on Human Gastric Cancer Cell Line Cytotoxic Effect of HSPI With/Without Mitomycin on Human Gastric Cancer Cell Line

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 94 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( x i ) SEQUENCE DESCRIPTION: SEQ ID NO:1:

```
Ser  Cys  Tyr  Phe  Ile  Pro  Asn  Glu  Gly  Val  Pro  Gly  Asp  Ser  Thr
1                 5                      10                         15

Arg  Lys  Cys  Met  Asp  Leu  Lys  Gly  Asn  Lys  His  Pro  Ile  Asn  Ser
                20                      25                         30
```

```
          Glu  Trp  Gln  Thr  Asp  Asn  Cys  Glu  Thr  Cys  Thr  Cys  Tyr  Glu  Thr
                             35                    40                        45

Glu  Ile  Ser  Cys  Cys  Thr  Leu  Val  Ser  Thr  Pro  Val  Gly  Tyr  Asp
                                  50                    55                        60

Lys  Asp  Asn  Cys  Gln  Arg  Ile  Phe  Lys  Lys  Glu  Asp  Cys  Lys  Tyr
                                  65                    70                        75

Ile  Val  Val  Glu  Lys  Lys  Asp  Pro  Lys  Lys  Thr  Cys  Ser  Val  Ser
                                  80                    85                        90

Glu  Trp  Ile  Ile
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:2:

```
          Tyr  Thr  Cys  Ser  Val  Ser  Glu  Trp  Gly  Ile
           1                  5                         10
```

( 2 ) INFORMATION FOR SEQ ID NO:3:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:3:

```
          Ser  Cys  Tyr  Phe  Ile  Pro  Asn  Glu  Gly  Val  Pro  Gly  Asp  Ser  Thr
           1                  5                        10                        15

Arg  Lys
```

( 2 ) INFORMATION FOR SEQ ID NO:4:

( i ) SEQUENCE CHARACTERISTICS:
        ( A ) LENGTH: 28 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:4:

```
          Ile  Phe  Lys  Lys  Glu  Asp  Cys  Lys  Tyr  Ile  Val  Val  Glu  Lys  Lys
           1                  5                        10                        15

Asp  Pro  Lys  Lys  Thr  Cys  Ser  Val  Ser  Glu  Trp  Gly  Ile
                            20                        25
```

PHARMACEUTICAL PREPARATIONS FOR INHIBITING TUMOURS ASSOCIATED WITH PROSTATE ADENOCARCINOMA

FIELD OF THE INVENTION

The present invention relates to pharmaceutical preparations for use as tumour suppressive agents for tumours arising from prostatic adenocarcinoma, stomach cancer, breast cancer and benign prostatic hyperplasia.

BACKGROUND OF THE INVENTION

The prostate gland, which is found exclusively in male mammals, produces several components of semen and blood and several regulatory peptides. The prostate gland comprises stroma and epithelium cells, the latter group consisting of columnar secretory cells and basal nonsecretory cells. A proliferation of these basal cells as well as stroma cells gives rise to benign prostatic hyperplasia (BPH) which is one common prostate disease. Another common prostate disease is prostatic adenocarcinoma (CaP) which is the most common of the fatal pathophysiological prostate cancers and involves a malignant transformation of epithelial cells in the peripheral region of the prostate gland. Prostatic adenocarcinoma and benign prostatic hyperplasia are two common prostate diseases which have a high rate of incidence in the aging human male population. Approximately one out of every four males above the age of 55 suffers from a prostate disease of some form or another. Prostate cancer is the second most common cause of cancer related death in elderly men with there being approximately 96,000 cases diagnosed and about 26,000 deaths reported annually in the United States.

Studies of the various substances synthesized and secreted by normal, benign and cancerous prostates carried out in order to gain an understanding of the pathogenesis of the various prostate diseases reveal that certain of these substances may be used as immunohistochemical tumour markers in the diagnosis of prostate disease. The three predominant proteins or peptides secreted by a normal prostate gland are Prostatic Acid Phosphatase (PAP), Prostate Specific Antigen (PSA) and prostatic inhibin (PIP) also known as human seminal plasma inhibin (HSPI) and hereinafter referred to as HSPI.

Metabolic and immunohistochemical studies have shown that the prostate is a major source of HSPI. HSPI is involved in the feedback control of, and acts to suppress secretion of, circulating follicle stimulating hormone (FSH) both in-vitro and in-vivo in adult male rats. HSPI acts both at the pituitary as well as at the prostate site since both are provided with receptor sites for HSPI.

Both PSA and PAP have been studied as tumour markers in the detection of prostate disease but since both exhibit elevated levels in prostates having benign prostatic hyperplasia (BPM) neither marker is specific and therefore they are of limited utility.

Recently, it has been shown that HSPI concentrations in serum of patients with BPH or CaP are significantly higher than normal. The highest serum concentration of HSPI observed in normal men is approximately 40 ng/ml., while in men with either BPH or CaP serum concentrations of HSPI have been observed in the range from 300–400 ng/ml. Because there exists some overlap in the concentrations of HSPI in subjects having normal prostates and patients exhibiting either BPH or CaP, serum levels in and of themselves are of little value.

A major therapy in the treatment of prostate cancer is androgen-ablation. While most patients respond initially to this treatment, its effectiveness decreases over time possibly because of the presence of a heterogenous population of androgen-dependant and androgen-independent cells to begin with. In such a scenario, the androgen sensitive cells respond to the androgen treatment while any androgen insensitive cells present would continue to proliferate unabated.

Other forms of cancer which are currently exacting a heavy toll are breast cancer in women and cancer of the gastrointestinal tract. Currently, the use of various cancer drugs such as mitomycin, idarubicin, cisplatin, 5-flouro-uracil, methotrexate, adriamycin and donomycin form part of the therapy for treating such cancers. One drawback to such a therapeutic treatment is the presence of adverse side effects due to the drugs in the concentration ranges required for effective treatment.

Accordingly, it would be advantageous to find a more effective means of arresting the growth of prostate, breast and gastrointestinal cancer cells and tumours which can be used effectively against both androgen sensitive and androgen insensitive cells.

SUMMARY OF THE INVENTION

In one aspect the present invention provides a method of inhibiting the growth of adenocarcinoma of the prostate using human seminal prostatic inhibin (Sequence ID No. 1) wherein the human seminal prostatic inhibin is administered to the prostate in a dosage range from about 500 picograms/kg/day to about 1 milligrams/kg/day.

In another aspect of the invention there is provided a method of inhibiting the growth of adenocarcinoma of the prostate using a decapeptide (Sequence ID No. 2) wherein the decapeptide is used in a dosage range from about 250 nanograms/kg/day to about
1 milligrams/kg/day.

The present invention provides a composition for the use of inhibiting adenocarcinoma of the prostate comprising human seminal prostate inhibin (Sequence ID No. 1) present in a dosage range of about 5 nanograms/kg/day to about 10 micrograms/kg/day and an anticancer drug.

LIST OF TABLES

Table I summarizes data showing the effect of HSPI administration on the serum levels of FSH and LH (ng/ml$^{-1}$) in intact adult male rats;

Table II summarizes data showing the effect of HSPI on cell proliferation;

Table III summarizes data showing the effect of HSPI on the weight (grams) of testes and prostate;

Table IV summarizes in-vivo data relating to HSPI dosage levels and subsequent tumour viability; and Table V summarizes data on various hormone levels measured in rats 14 days after treatment with two different levels of HSPI.

BRIEF DESCRIPTION OF THE DRAWINGS

The invention will be described, reference being had to the drawings, in which:

FIG. 1 shows the complete sequence of human HSPI (Sequence ID No. 1)

FIG. 11 illustrates the R-10 peptide (Sequence ID No. 2) in the box which are the last 10 amino acids of HSPI (Sequence ID No. 1) but with lysine in position 85 replaced by tyrosine;

FIG. 12 illustrates the R-17 peptide (Sequence ID No. 3) as it appears in HSPI (Sequence ID No.1) and the R-28 peptide (Sequence ID No. 4) as it appears in HSPI.

FIG. 13 summarizes the data of Table IV in bar graph form; and

DESCRIPTION OF THE INVENTION

The inventors have considered that high levels of HSPI (Sequence ID No. 1) under pathophysiological conditions associated with prostate cancer may serve as a form of defence mechanism, albeit apparently not always effective, which may be initiated by the prostate. Various in-vivo and in-vitro experimental studies have been carried out and are summarized herebelow to determine the efficacy of concentrations of HSPI (Sequence ID No. 1) higher than concentrations secreted by the diseased prostate as tumour suppressive agents for arresting or inhibiting the growth of prostatic adenocarcinoma. Studies have also been carried out to determine the efficacy of synthetic analogues of HSPI, (Sequence ID No. 1) specifically peptides having 10 amino acids (Sequence ID No. 4), 17 amino acids (Sequence ID No. 3) and 28 amino acids (Sequences ID No. 4), as tumour suppressive agents. These synthetic analogues have been shown to closely mimic the action of HSPI (Sequence ID No. 1) in suppressing circulating FSH levels preferentially without altering the levels of luteinizing hormone (LH).

Figure 10:
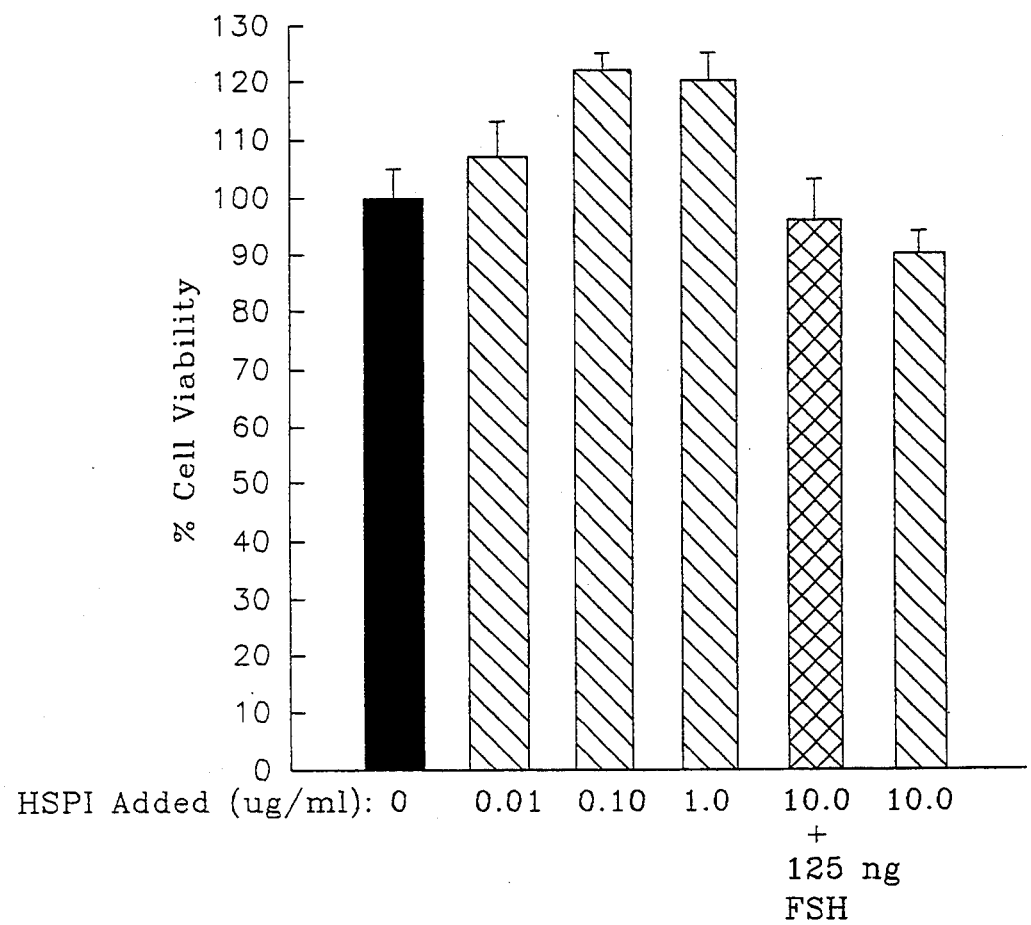
FIG. 10 summarizes studies of the effect of FSH on prostate cancer cell growth in-vitro and its inhibition by HSPI (Sequence ID No. 1)
Figure 14:
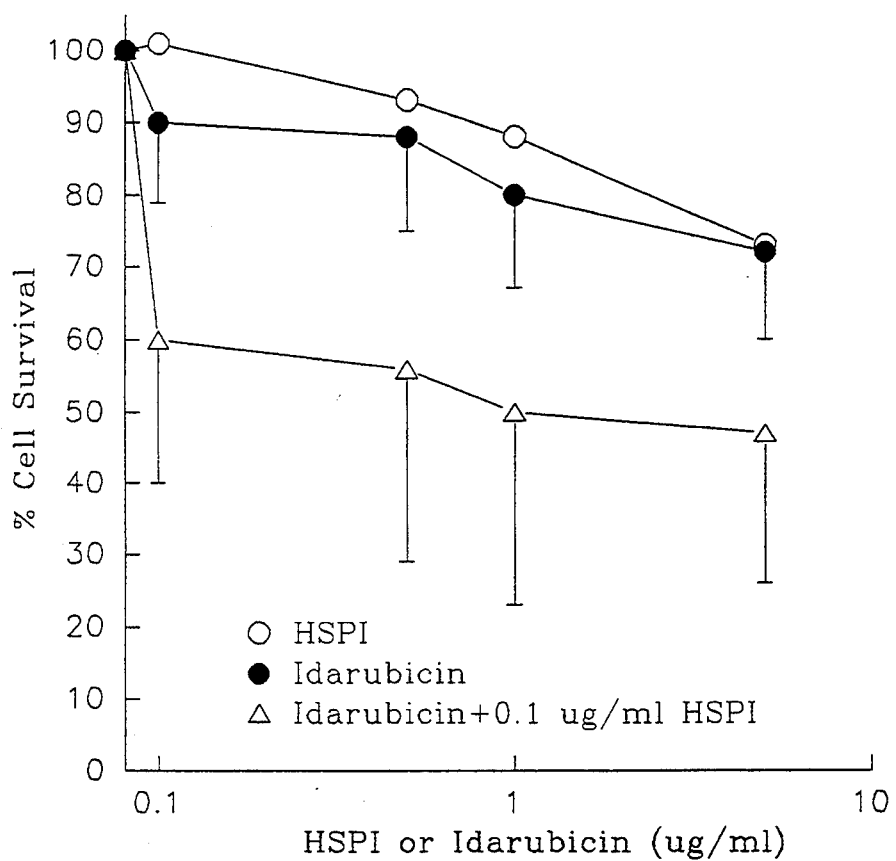
FIG. 14 illustrates the cytotoxic effect of HSPI (Sequence ID No. 1) with and without the anticancer drug idarubicin on the human gastric cancer cell line.
Figure 15:
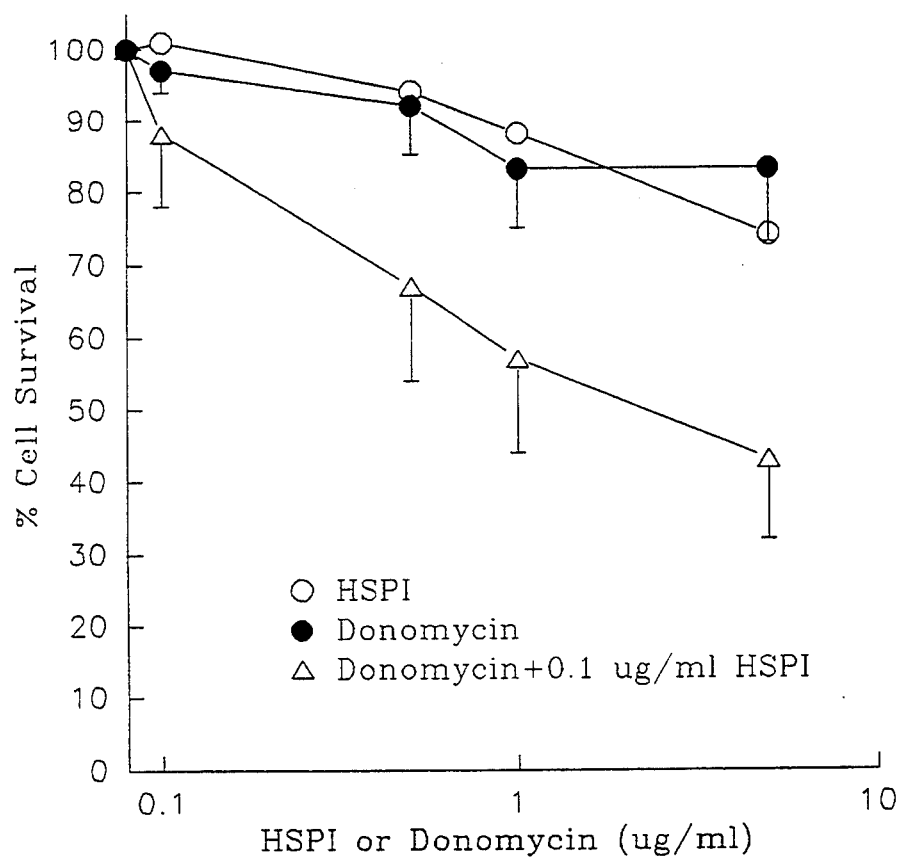
FIG. 15 illustrates the cytotoxic effect of HSPI (Sequence ID No. 1) with and without the anticancer drug daunomycin on the human gastric cancer cell line.
Figure 16:
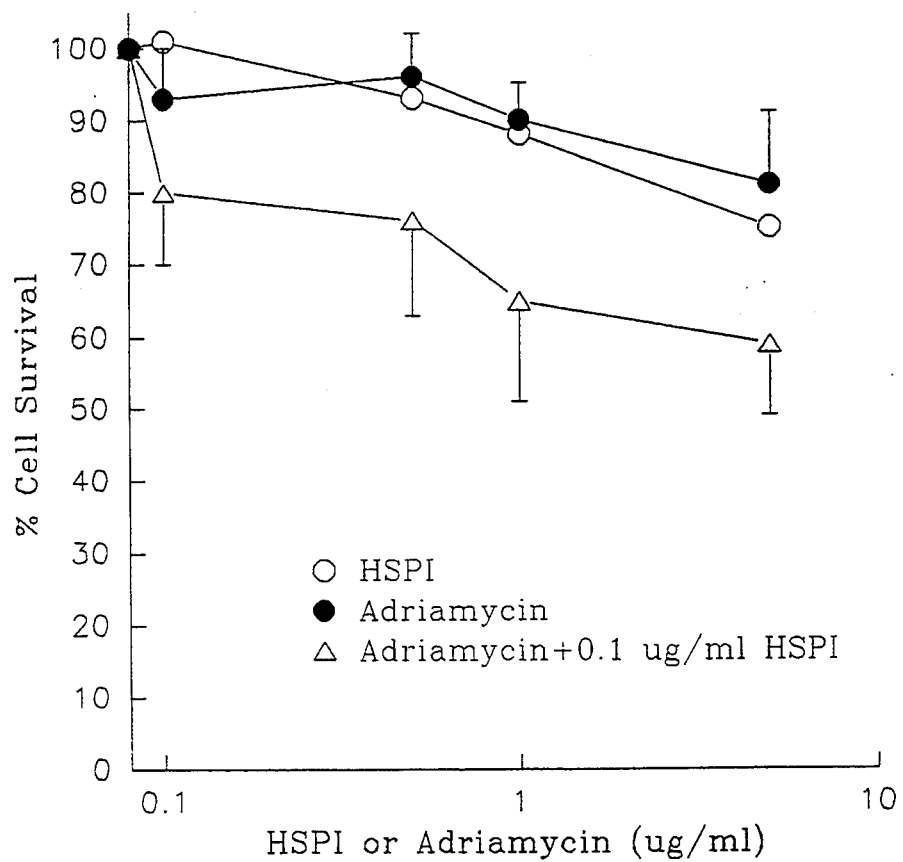
FIG. 16 illustrates the cytotoxic effect of HSPI (Sequence ID No. 1) with and without the anticancer drug adriamycin on the human gastric cancer cell line.
Figure 17:
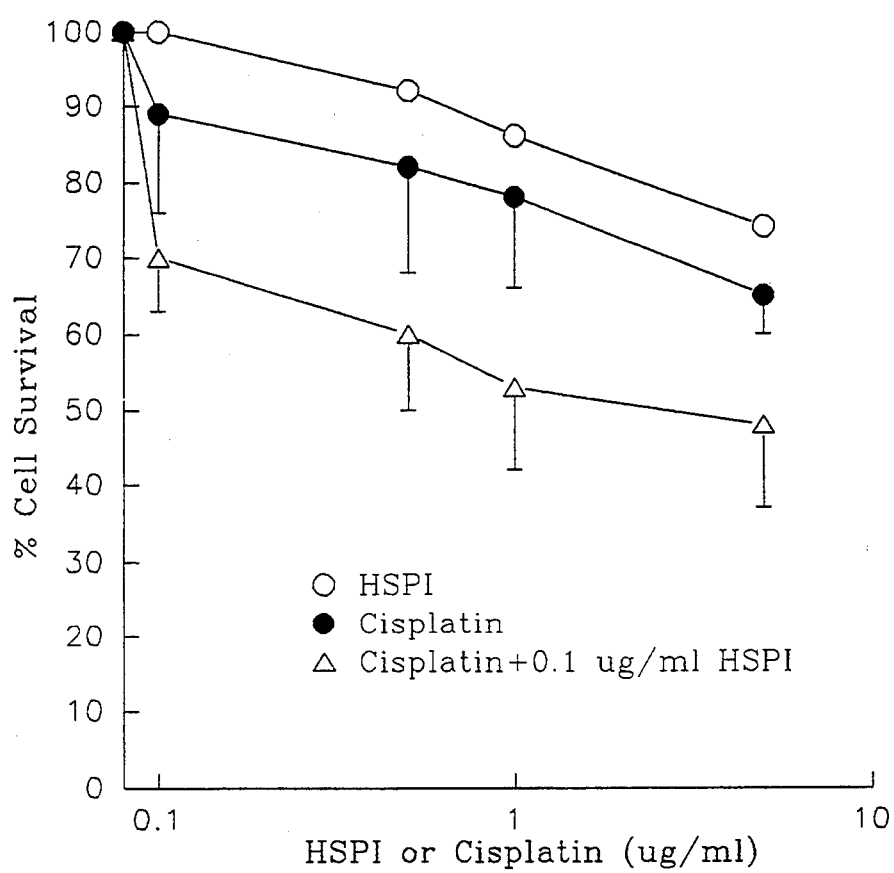
FIG. 17 illustrates the cytotoxic effect of HSPI (Sequence ID No. 1) with and without the anticancer drug cisplatin on the human gastric cancer cell line.
Figure 18:
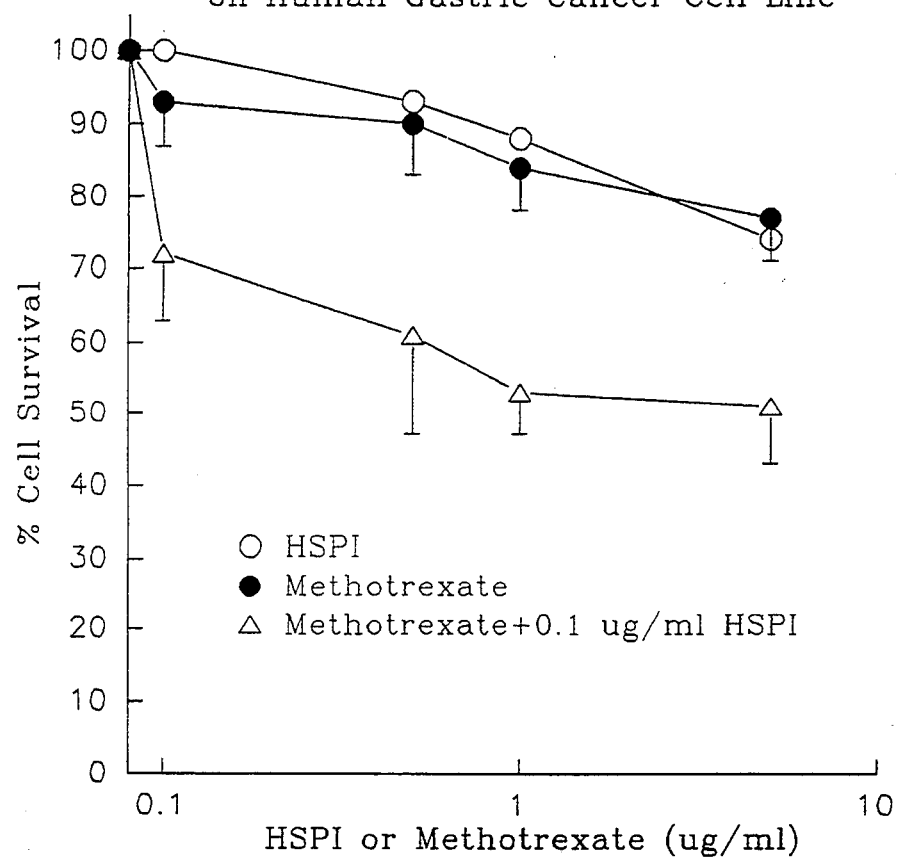
FIG. 18 illustrates the cytotoxic effect of HSPI (Sequence ID No. 1) with and without the anticancer drug methotrexate on the human gastric cancer cell line.
Figure 19:
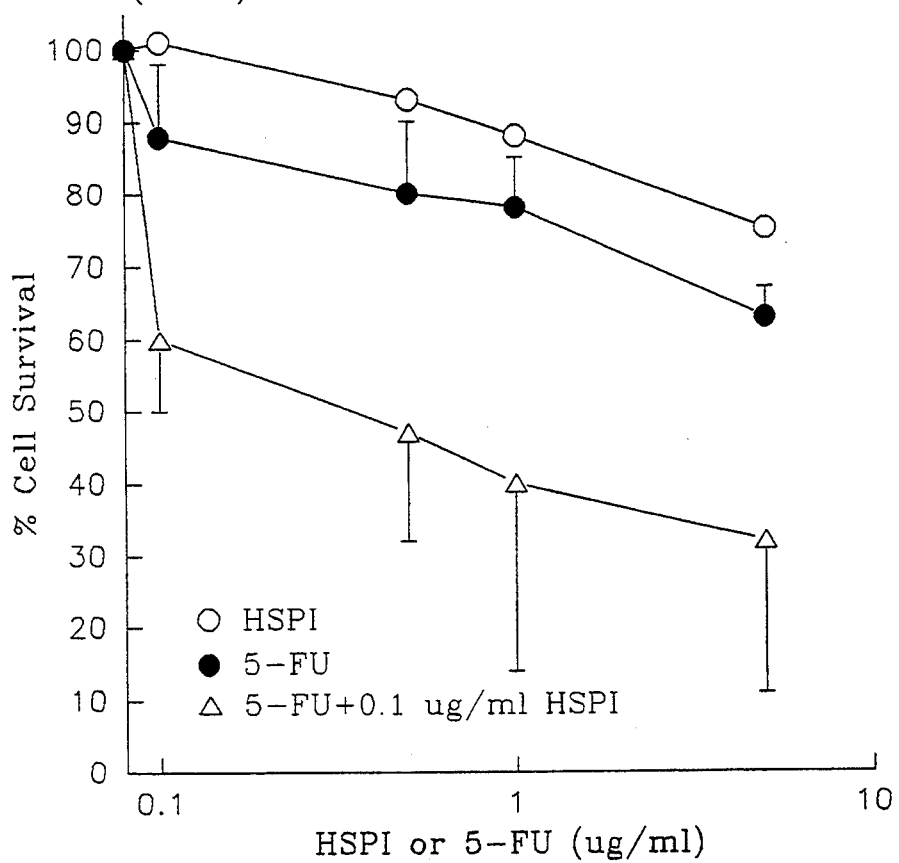
FIG. 19 illustrates the cytotoxic effect of HSPI (Sequence ID No. 1) with and without the anticancer drug 5-fluoro-uracil (5-FU) on the human gastric cancer cell line.
Figure 20:
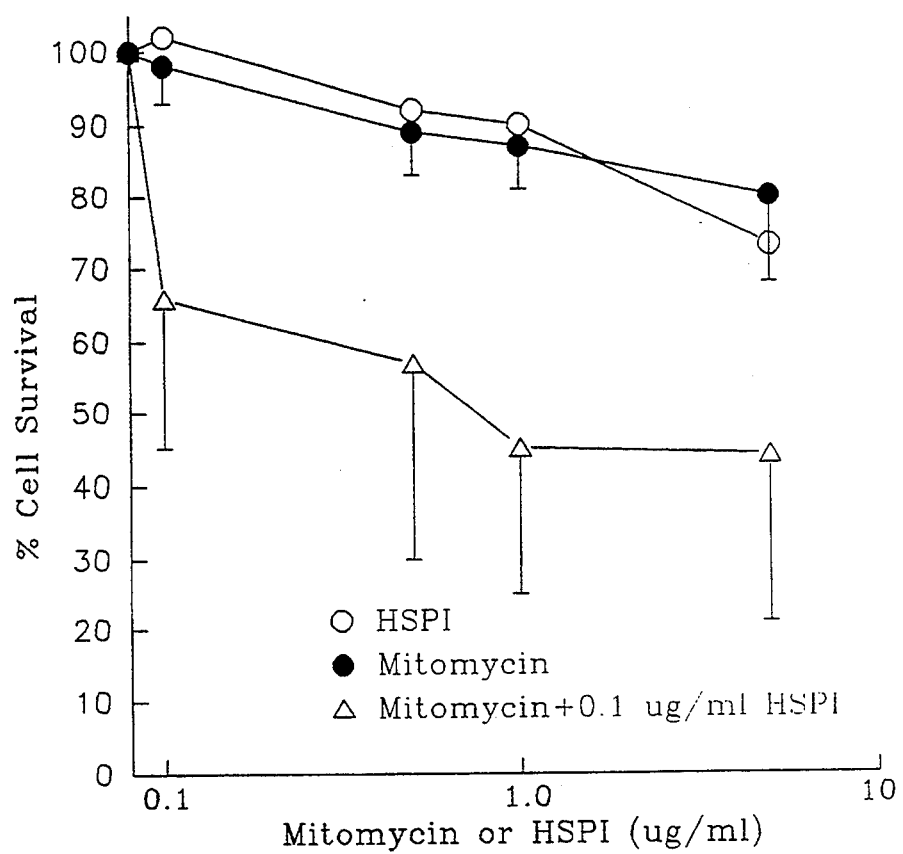
FIG. 20 illustrates the cytotoxic effect of HSPI (Sequence ID No. 1) with and without the anticancer drug mitomycin on the human gastric cancer cell line.

The bar graph of FIG. 10 summarizes studies of the effect of FSH on prostate cancer cell growth in-vitro and its inhibition by HSPI (Sequence ID No. 1). The tumour cells were exposed for 48 hours to HSPI with 0.5% serum in tissue cultures.

PREPARATION OF HSPI

Referring to FIG. 1, HSPI (Sequence ID No. 1) is a simple nonglycosylated protein comprising at least 94 amino acid residues. HSPI produced by the prostate has a molecule weight of approximately 10.7 kDa.

Figure 2:
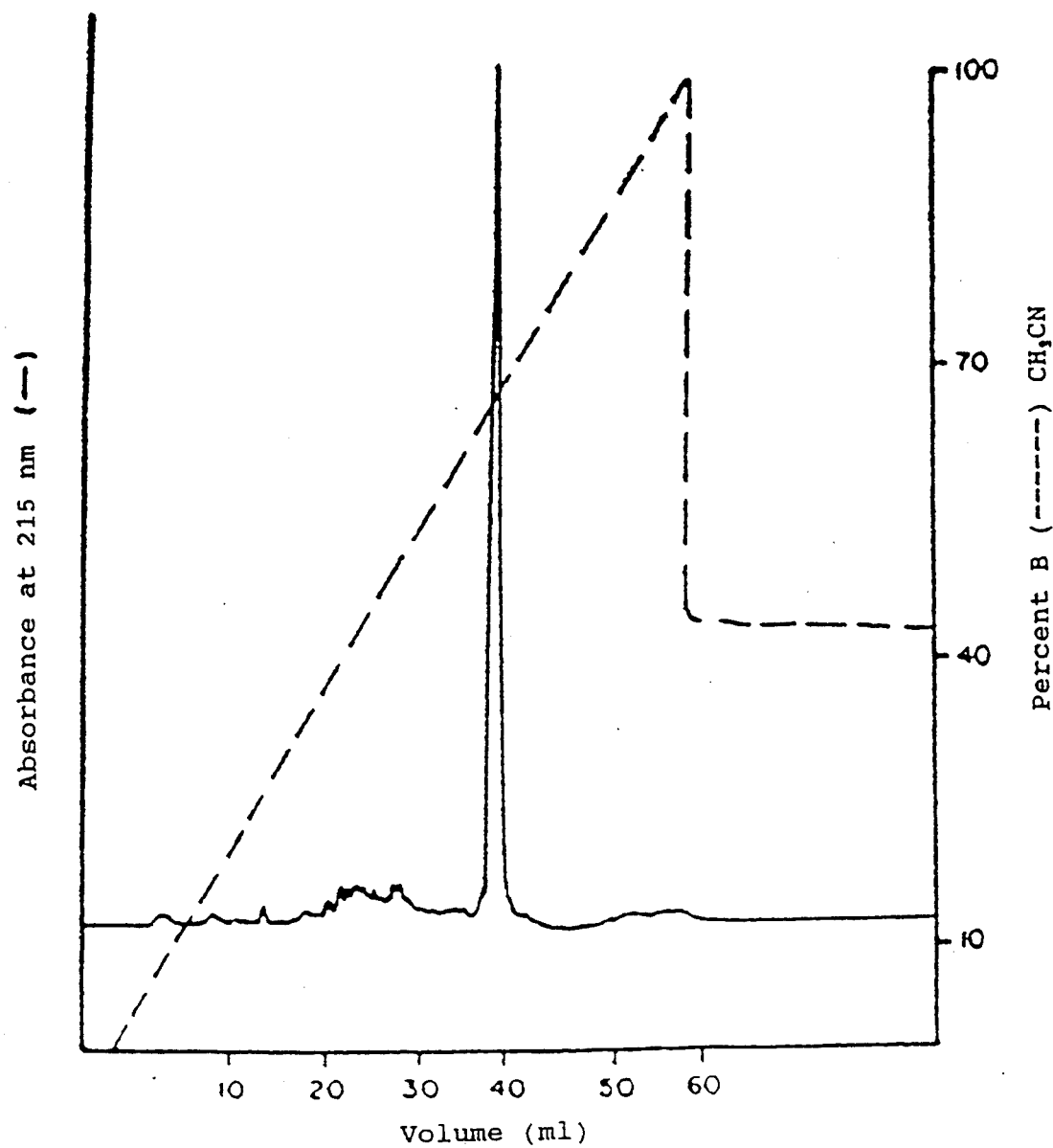
FIG. 2 illustrates an HPLC profile of HSPI (sequence ID no. 1) on a gel permeation column (LKB-TSK G 3000 SW 7.5×600 mm), the material being eluted as a major peak.

HSPI (Sequence ID No. 1) antigen was purified according to the basic procedure of Thakur et al (1981) ISOLATION AND PURIFICATION OF INHIBIN FROM HUMAN SEMINAL PLASMA, Indian Journal of Experimental Biology, 19, 307–313 but with modifications (Thakur et al. and Sheth et al. (1984) CHARACTERIZATION OF A POLYPETIDE FROM HUMAN SEMINAL PLASMA WITH INHIBIN (INHIBITION OF FSH SECRETION)-LIKE ACTIVITY, FEBS Letters, 165, 11–15.). Sperm-free human seminal plasma was precipitated with alcohol (1:4 vol/vol) and then extracted with 0.05M acetate buffer, pH 4.0. The soluble proteins were separated using chromatography on a Sephadex G-100 column (3.5×100 cm) using 0.01M acetate buffer for equilibrium and elution. The fraction with FSH-suppressing activity was subjected to ion-exchange chromatography on DEAE-cellulose (3×30 cm). The column was washed initially with 0.05 Tris buffer, pH 8.0. The bound material was eluted using an NaCl gradient (0–0.5M) in the same buffer. The active material collected was subsequently purified by high pressure liquid chromatography (HPLC) using a gel permeation column (LKB-TSK G-3000 S.W., 7.5×600 mm) and 0.01M acetate buffer, pH 4 for equilibration and elution, see FIG. 2.

Figure 3:
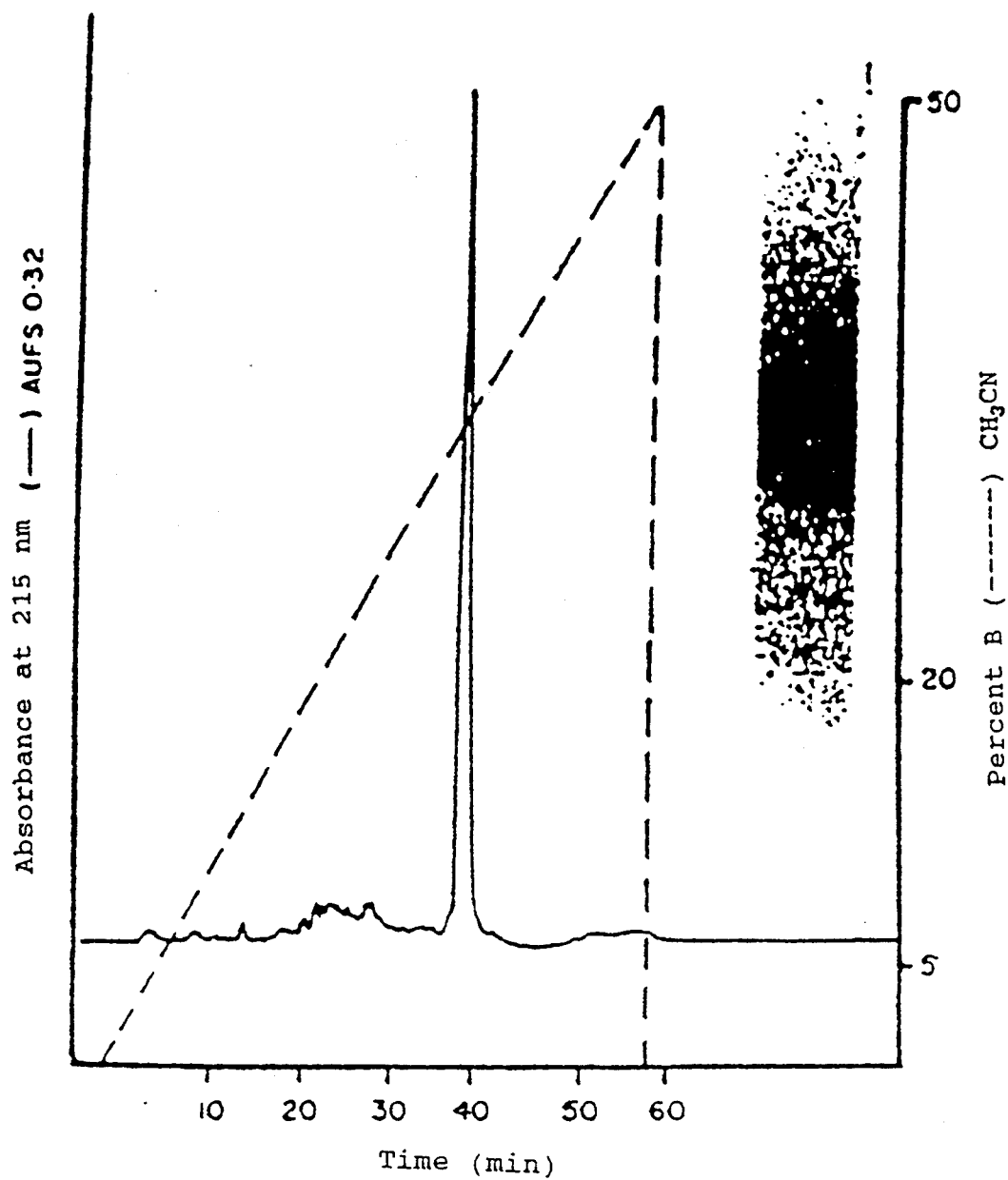
FIG. 3 illustrates a reverse phase HPLC of purified HSPI (Sequence ID no. 1) on a column of Lichrosorb RP-18 (5 μm; 0.4×25 cm, eluant, A 0.1% (w/v) aqueous TFA; B, 50% $CH_3CN$ in 0.1% aqueous TFA; Flow rate, 1 ml/min, inset: SDS gel electrophoresis pattern of purified HSPI (method of Laemmli, 1970)

The HPLC purified material exhibited a single band on SDS-Gel electrophoresis at pH 8.3 (see inset of FIG. 3). On reverse phase HPLC, the purified material eluted as a single peak, see FIG. 3.

The fractions obtained at each stage of purification were assayed for bioactivity using intact adult male rats. The assay is based on suppression of circulating FSH levels. Administration of HPLC-purified HSPI (Sequence ID No. 1) to adult male rats for 3 consecutive days caused specific suppression of circulating FSH levels, see Table 1. No significant change in LH levels was observed.

SYNTHESIS OF DECAPEPTIDE HSPI ANALOGUE

The decapeptide analogue of HSPI pep forming part of the subject invention disclosed herein is a synthetic analogue of the 85-94 amino acid residues at the carboxy terminal of the HSPI sequence. The decapeptide (Sequence ID No. 2) differs from HSPI (Sequence ID No. 1) in that the lysine residue at position 85 in HSPI (Sequence ID No. 1) is replaced by a tyrosine residue and the cysteine residue at position 87 is protected by an acetomidomethyl group. This synthetic decapeptide (Sequence ID No. 2) and other fragments were prepared using an Automated Peptide Synthesizer.

IN-VITRO AND IN-VIVO STUDIES

Studies were carried out using the rat Dunning R-3327-G tumour which is a pre-eminent animal model for the study of CaP. The Dunning tumour is a fast growing, poorly differentiated, transplantable tumour which can be maintained both in-vivo in the Copenhagen x Fisher 344 rat and in-vitro as a cell line.

EXPERIMENT 1

EFFECT OF HSPI ON IN-VITRO CELLS

Dunning tumour R-3327-G lines derived from cells dissociated in their 20th and 28th in-vivo passages in Copenhagen x 344 male carrier rats were used for the in-vitro studies. Tumours were excised and dissociated into single cells and cultured in T-25 culture flasks (Corning N.Y.). Dissociated tumour cells were dislodged from the culture flask by trypsinization (0.25% trypsin and 0.02% EDTA at 37° C. for 3 minutes) and passaged in alpha-MEM (GIBCO Labs, Grand Island, N.Y.) supplemented with 2 mM L-glutamic acid, 20% fetal bovine serum (FBS, Hyclone Labs., Logan, Vt.) and antibiotics (complete medium=CM). Cultures were passaged every five days.

For colony assay, R-3327-G cells between 2 and 10 in-vitro passages were trypsinized, dispersed into single cell suspension and cultured in 35 mm tissue culture dishes at $0.5-1.0 \times 10^1$ viable cells in 2 ml CM. Propep was diluted at various concentrations in CM, filtered, sterilized and then added at appropriate concentration to culture dishes. These culture dishes were incubated in a humidified incubator at 37° C. with 5% $CO_2$ for seven days. Following this the culture dishes were emptied, washed twice in cold phosphate buffer saline (PBS) solution and then fixed in absolute methanol for 5 minutes. The culture dishes were then stained with acidified Harris Hematoxylin and the colonies were counted manually.

Figure 4:
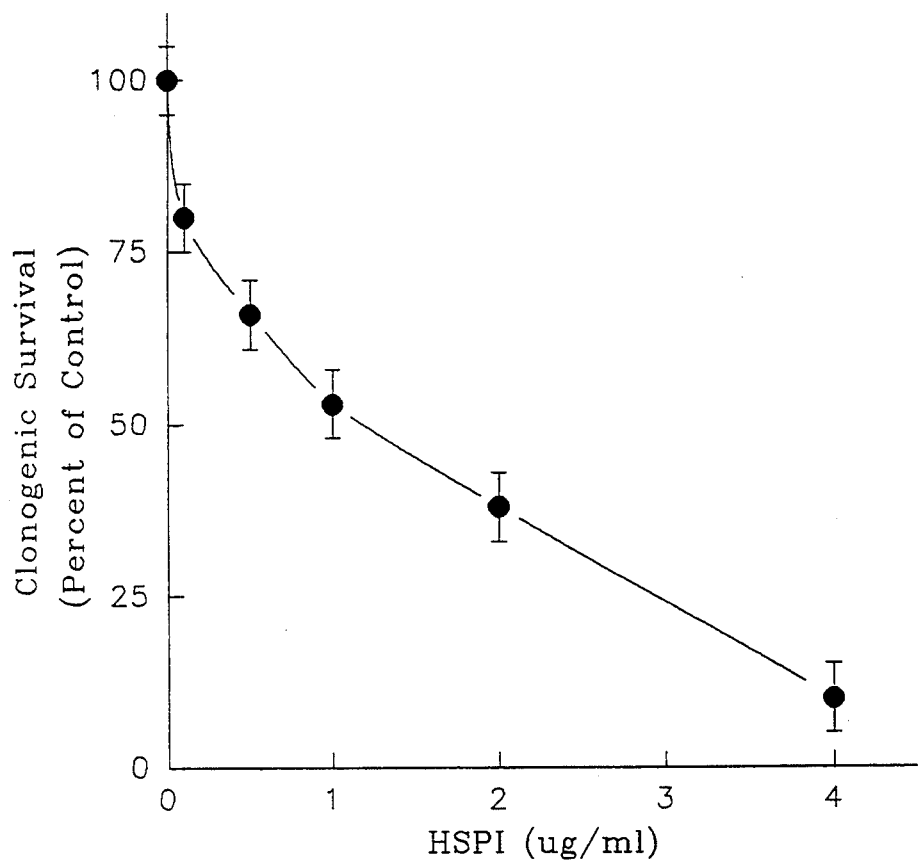
FIG. 4 displays the % survival of Dunning tumor R-3327-G cell lines on concentration of HSPI (Sequence ID No. 1)

Between about 20% to 30% of plated R-3327-G cells formed characteristic diffuse colonies within 7 days. Typically, colonies consisted of 102.3±13.7 cells. A dose dependent inhibition of both colony number and colony size were observed with addition of various concentrations of HSPI. Above concentrations of 100 ng/ml the colony inhibition was significant, leading to a 50% reduction at a HSPI (Sequence ID No. 1) concentration of 1 μg/ml. Increasing concentrations of HSPI (Sequence ID No. 1) resulted in small cell-clusters (50 cell-FIG. 4). Replenishing the culture media along with the HSPI (Sequence ID No. 1) on the 4th day of the culture resulted in more effective and consistent inhibition of colony growth than that of one time HSPI (Sequence ID No. 1) addition.

EXPERIMENT 2

EFFECT OF DECAPEPTIDE AND OTHER FRAGMENTS ON IN-VITRO CELLS

Figure 5:
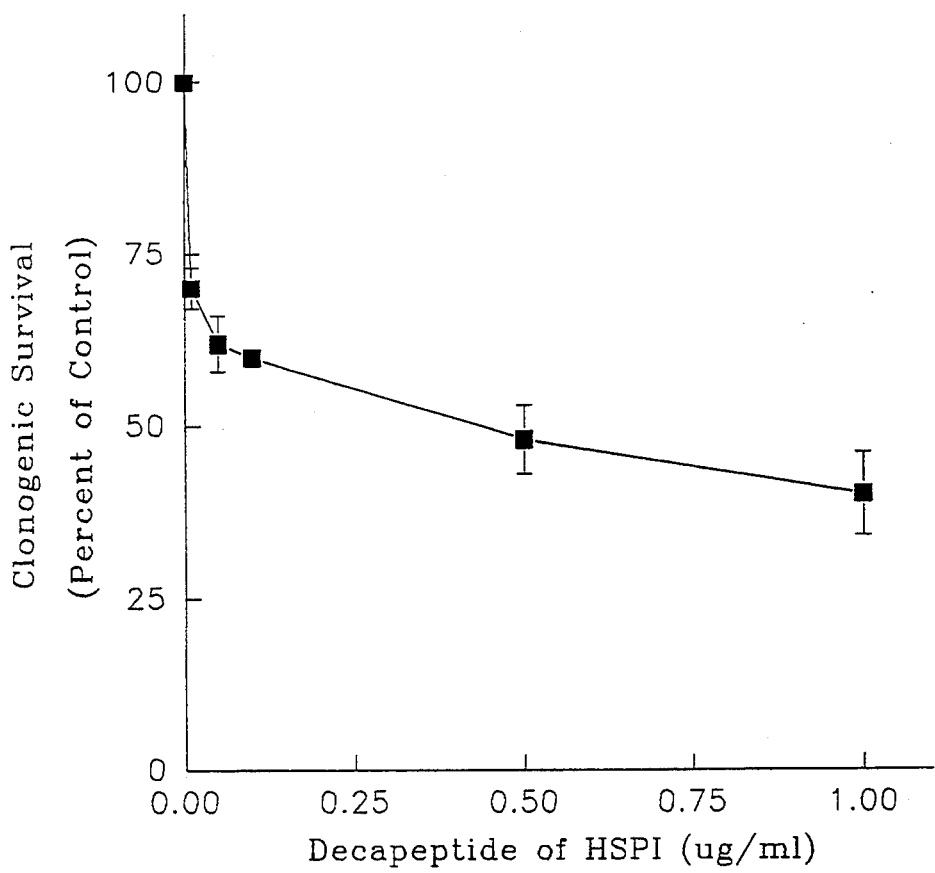
FIG. 5 displays the % survival of Dunning tumour R-3327-G cell lines on concentration of the decapeptide analogue (Sequence ID No. 2)

The synthetic decapeptide (Sequence ID No. 2) shown in the box in FIG. 11 has been shown to mimic the biological action of HSPI (Sequence ID No. 1) and therefore its effect on the R-3327-G cells was studied. Referring to FIG. 5, the decapeptide (Sequence ID No. 2) has a similar inhibitory action as HSPI (Sequence ID No. 1) on in-vitro R-3327-G cell culture. Specifically, a 50% colony count inhibition was observed with 50 ng/ml of the decapeptide (Sequence ID No. 2) leading to a maximum of 70% inhibition at 1 μg/ml. However, referring again to FIG. 4, an equimolar concentration of the native HSPI (Sequence ID No. 1) was found to have a greater inhibiting effect compared to the decapeptide (Sequence ID No. 2). Other peptides having 17 amino acids (Sequence ID No. 3) and 28 amino acids (Sequence ID No. 4) see FIG. 12, have demonstrated a similar efficacy for suppressing FSH levels, data not shown.

EXPERIMENT 3

EFFECT OF HSPI ON ANDROGEN DEPENDENT AND INDEPENDENT R-3327-G IN-VITRO CELL COLONIES

The R-3327-G tumours comprise both androgen sensitive and androgen insensitive cells. The effect of HSPI (Sequence ID No. 1) on these two cell populations was studied in-vitro. Cells were dissociated from a R-3327-G tumour in its 20th in-vivo passage and were cultured in the presence or absence of steriods. For comparison, cells from the 28th in-vivo passage known to be largely androgen insensitive were cultured in the same way.

Figure 6:
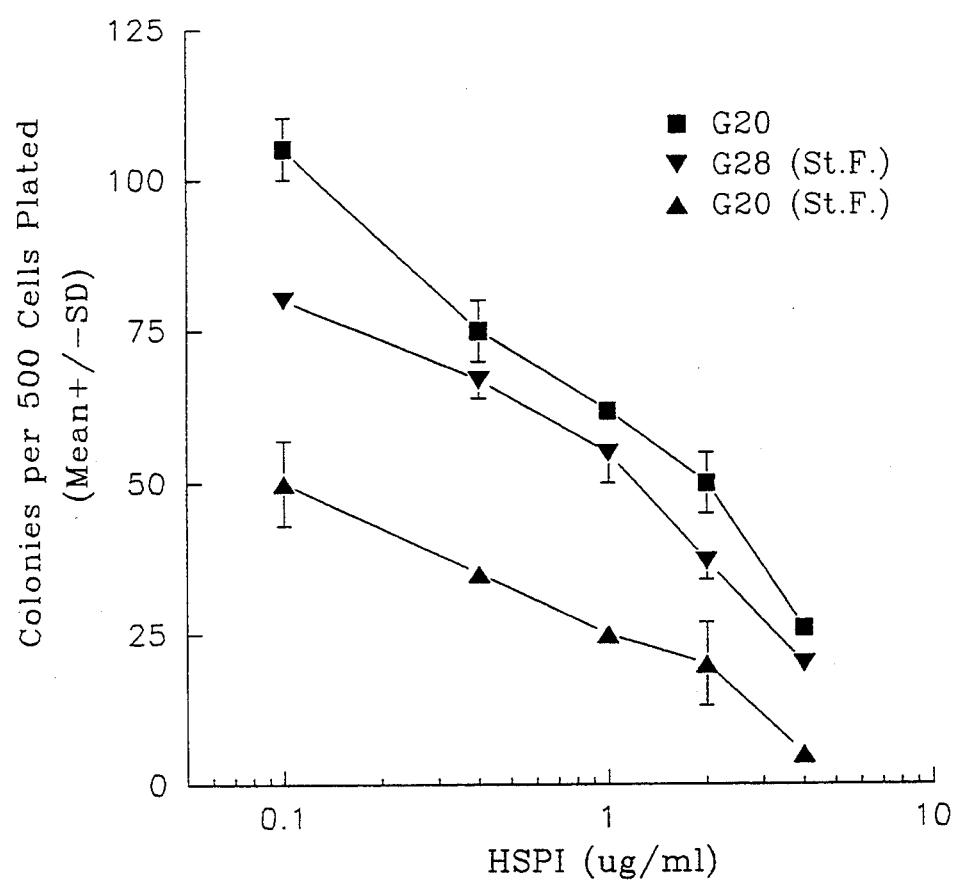
FIG. 6 shows the effect of various concentrations of HSPI (Sequence ID No. 1) on the growth of R-3327-G cells.

The results of the effect of various concentrations of HSPI (Sequence ID No. 1) on the in-vivo cells is summarized in FIG. 6. The effect of propep was similar under all test conditions for both androgen sensitive and androgen insensitive cells. Although the actual number of colonies which appeared under each assay condition were different with these cells, the extent of propep induced colony inhibition was comparable in all.

EXPERIMENT 4

INHIBITION OF CELL-GROWTH BY HSPI

Colony inhibition might occur as a result of immediate cell death or due to delay in the cell cycle. In order to distinguish between these two routes of inhibition, the following experiment was conducted.

Aliquots of $0.5 \times 10^1$ cells were cultured in 24 well plates and incubated with various concentrations of HSPI (Sequence ID No. 1). Cell counts were taken on days 3 and 7. In control wells the number of cells increased 4-fold after 3 days and 28-fold after 7 days. At a dose of HSPI (Sequence ID No. 1) of 1 μg/ml, no increase in cell number was observed on day 3 while only a 5-fold increase was observed on day 7, see Table II.

Figure 7:
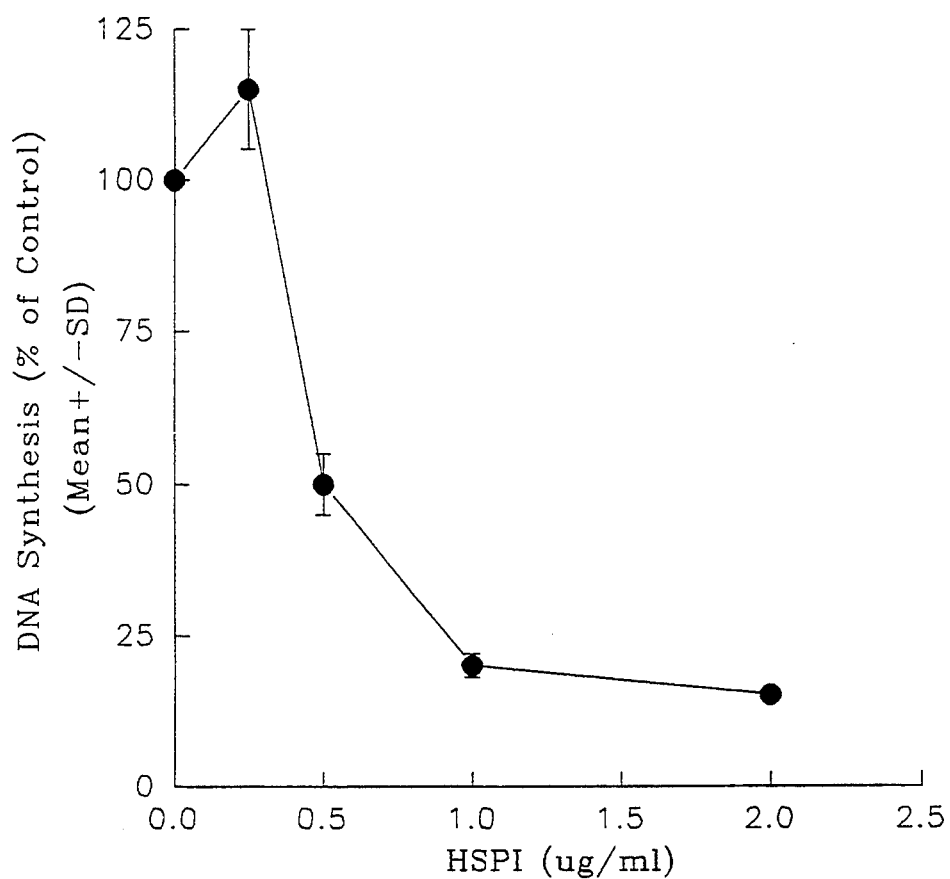
FIG. 7 displays the patterns of DNA synthesis in R3327-G cells treated with and without HSPI, as depicted by $^3$H-thymidine incorporation.

The results of this study were further corroborated by measuring DNA synthesis using 3H-thymidine. Specifically, R-3327-G cells were cultured in 24-well tissue culture plates (Costar, Mass.) in the presence or absence of HSPI (Sequence ID No. 1) for six days. 3H-thymidine (68 Ci/mmole, ICN Ca) diluted in CM containing 10 μM thymidine (Sigma MO) was added to duplicate culture wells (0.5 μCi/ml). Plates were further incubated for 18 hrs. The amount of 3H-thymidine incorporated was estimated by precipitation with trichloro acetic acid, as described previously. FIG. 7 shows patterns of $^3H$ thymidine incorporation in HSPI incubated cultures on day 7, as depicted by DNA synthesis. Cultures that received HSPI (Sequence ID No. 1) in the amount of 1 μg/ml had incorporated by day 7 only about 20% of radioactivity as compared to that of the control. The inhibitory effect of the HSPI (Sequence ID No. 1) was more pronounced on day 7 than on day 3.

EXPERIMENT 5

IN-VIVO EXPERIMENT

Copenhagen x Fisher 344 F hybrid male rats were ear-tagged and implanted with R3327-G cells ($1 \times 10^1$ cells/animal in the 28th in-vivo passage) as described earlier. The animals weighed approximately 500 grams at the time of tumour implantation. A treatment regimen was initiated when tumour volume measured 0.2 to 0.5 cc.

Tumour bearing animals were divided into two groups of eight. One group comprising the control group, received saline injection while the other group received HSPI (Sequence ID No. 1) dissolved in saline in the amount of 5 μg/kg subcutaneously every day.

The tumour volume was approximated by 3-dimensional measurement using the formula $0.5236 \times length \times width \times depth$. The rats were sacrificed 24 days after tumour implantation as control tumours at that point in time started becoming necrotic. Accessory sex organs and tumours were excised from the rats and weighed.

Figure 8:
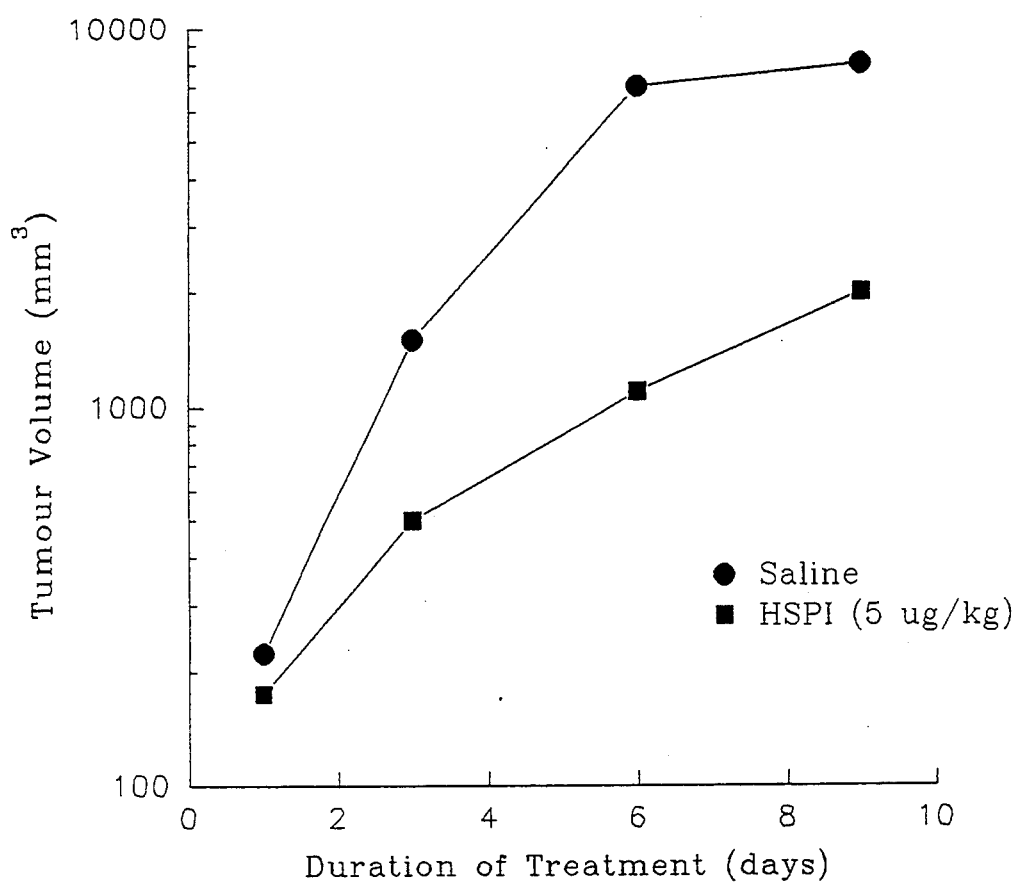
FIG. 8 displays the effect of HSPI (Sequence ID No. 1) on tumour volume in Dunning rats.

Significantly reduced tumour growth was observed in animals treated with HSPI (Sequence ID No. 1) as compared to that of the saline group. Referring to FIG. 8, the difference between the tumour volume in the control group and the HSPI (Sequence ID No. 1) treated group became increasingly pronounced with longer treatment. As tumours in the control group started to become necrotic on day 24, tumour and accessory sex organs were excised and weighed on this day. Mean tumour weight of the HSPI incubated group was $2.66 \pm 0.48$ g as compared to $6.44 \pm 1.19$ g for the saline treated control group. A 58% reduction in tumour weight was observed at the end of the experiment i.e. on the 24 day following tumour implantation or on the 10th day following administration of HSPI (Sequence ID No. 1) as compared to the saline treated control group. No significant change was observed in testes weight and prostate weight in HSPI (Sequence ID No. 1) treated group, see Table III.

EXPERIMENT 6

IN-VIVO EXPERIMENT

The tumour bearing animals were divided into three group of 8 animals. The first group was the control group and received saline treatment. The second group received HSPI (Sequence ID No. 1) in the amount of 5 μg/kg and the third group received 1000 μg Leuprolide TM /kg. This treatment regimen continued until the tumour volume for each animal reached approximately 10 cc. Tumour volumes were measured twice a week as described earlier.

The tumour volume data for each individual tumour was log transformed. Statistical analysis between treated and control group was performed by student "t" test.

Figure 9:
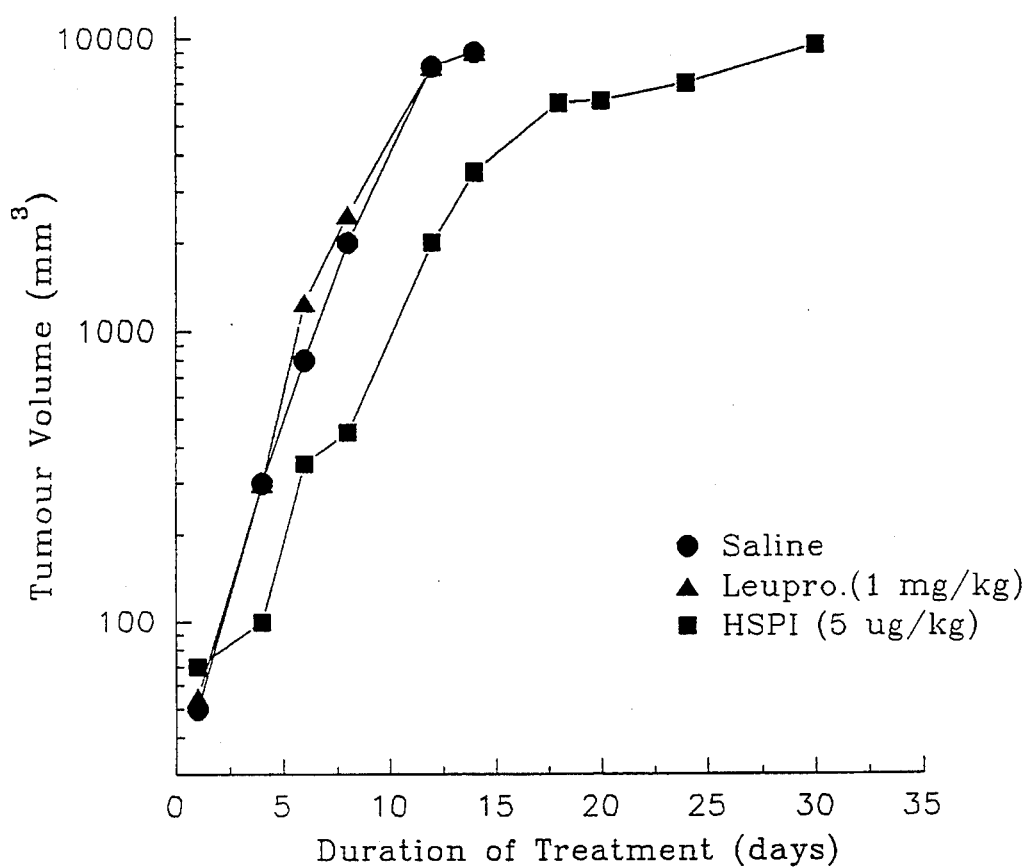
FIG. 9 shows a comparison of tumour volume as a function of duration of treatment with saline, leuprolide and HSPI (Sequence ID No. 1);.

As these results clearly demonstrated a growth inhibition following administration of HSPI (Sequence ID No. 1), the study was further extended to estimate tumour growth delay in Propep treated animals. Most of the tumours become necrotic by the time they reach 10 cc volume, following which the measurements may not be accurate thus, keeping this in mind, 10 cc was taken as an end point in this study. Among 8 animals in the treated group, tumour volume in 6 reached 10 cc by day 42 and in 2 by day 38. In the saline control group, tumour volume reached this size by day 30, see FIG. 9. In other words, a delay of 10 days in tumour growth was observed in the Propep treated animals. In all experiments the difference in tumour growth rate curves of treated and control groups of animals was similar.

The cells used for the foregoing experiment were from the 28th in-vivo passage, which is a poorly differentiated androgen-insensitive tumour. In order to confirm this earlier observation, one group of animals were treated with Leuprolide TM which is an anti-androgen. There was no significant difference in the tumour growth rate of in animals treated with lueprolide TM as compared to the saline control group.

EXPERIMENT 7

IN-VIVO EXPERIMENTS USING MAT-LYLU CELL LINES

The androgen independent Dunning rat adenocarcinoma cell lines, Mat-Lylu were obtained from Dr. J. T. Isaacs, Johns Hopkins Medical School, Baltimore, Md. and cultured in the laboratory by using RPMI 1640 medium containing 10% fetal calf serum and 1% antibiotics. When the cells reached confluency, they were trypsinized, dispersed into single cell suspension and the cell count was taken using hemocytometer.

Tumours were induced in adult Copenhagen male rats weighing about 200 gms by subcutaneous injection of $2 \times 10^6$ cells on two sides of the flank area. Animals were segregated into different groups and the HSPI (Sequence ID No. 1) injections were initiated on day 4 following the induction of tumour growth. Table IV shows the various concentrations HSPI (Sequence ID No. 1) injected into the animals.

Animals were injected every day and sacrificed on day 14 following the administration of tumour cells. The body weight and the tumour weights were recorded for both control and treated groups. Blood was collected through a cardiac puncture and serum FSH, LH, prolactin, testosterone and HSPI (Sequence ID No. 1) were measured by radio immunoassay. These serum levels of the above mentioned hormones are summarized in Table V for the control group and animals treated with dosages of 5 ng and 50 ng of HSPI (Sequence ID No. 1). These results show that FSH levels decrease with dosage which suggests the mechanism of action of HSPI (Sequence ID No. 1) relates to levels of FSH. In addition, testosterone levels are not adversely affected which indicates no loss of libido, in contrast to libido loss observed with current drugs used in the treatment of prostate and other forms of cancer.

A piece of tumour tissue from each animal was fixed in 10% buffered formalin to study the morphology of the cells. Table V shows the % viability of the tumours in treated groups when compared to the controls (100%). The results of table IV are summarized in the bar graph of FIG. 13.

The foregoing studies show that HSPI (Sequence ID No. 1), when administered in a predetermined concentration range, results in a significant inhibition, in-vivo of cancerous tumours associated with the prostate. Specifically, the Dunning rat studies with propep show that an effective drug dosage "window" of between about 5 ng to 500 ng per 200 grams body weight exists. These results have been corroborated by several studies.

Those skilled in the art will be aware of the methods of preparing pharmaceutically appropriate dosage forms for HSPI as applied to humans. Those skilled in the art will also appreciate that such dosages may be encapsulated and delivered using slow release technology comprising for example a liposome delivery system, polysaccharides exhibiting a slow release mechanism, salistic or other polymer implants or microspheres.

EXPERIMENT 9

STUDY OF THE EFFECT OF HUMAN SEMINAL PROSTATE INHIBIN (SEQ ID NO 1) ON FRESH GASTRIC TUMOUR CELLS IN-VITRO BY METHYL TETRAZOLIUM SALT (MTT) ASSAY

Gastric tumour specimens were collected from patients with stomach cancer undergoing gastrectomy at Tata Memorial Hospital. Tumour specimens were collected in sterile DMEM and immediately transferred to the laboratory under cold conditions. The gastric tumour specimens were finely minced with a sterile pair of scissors. The finely minced gastric tissue was incubated with 1% collagenase 1 and IV in Dulbeco's minimum essential medium (DMEM) with 10% fetal calf serum (FCS) at 37° C. with 5% $CO_2$ in an incubator for 1 hr. The whole mixture was then passed through a Millipore filter assembly and wire mesh (30 $\mu$m size) to get a single cell suspension of gastric tumour cells. The cells obtained were further subjected to primary culture in sterile culture bottles in 50 ml DMEM with 10% FCS and incubated for 12-18 hr. at 37° C. with 5% $CO_2$ in an incubator, with 10 $\mu$l of 0.1, 0.5, 1.0, and 5.0 $\mu$g/ml concentration of HSPI (Sequence ID No. 1) in a sterile 96 well microtitre plate. Blank and control in 6 microwells each were run along with tests. The plate was further incubated for 48 hrs. at 37° C. in 5% $CO_2$. After 48 hrs., 10 $\mu$l of 5 mg/ml MTT was added in each well. After 6 hrs. of incubation at 37° C., 100 $\mu$l of 1N HCl:Isopropanol (1:25) was added to each well and mixed vigorously to dissolve the farmazan crystals. Absorbance values at 540 nm were determined on an ELISA reader. Blank values were subtracted from the control and test values.

The percentage cell survival for each concentration HSPI (Sequence ID No. 1) along with concentrations of known 1) anticancer drugs used in the treatment of gastric cancer including cisplatin, 5-fluoro-uracil, methotrexate, mitomycin, and 2) other anticancer drugs used in chemotherapy including idarubicin, adriamycin, doxorubicin, and daunomycin and combinations of HSPI (Sequence ID No. 1) and these anticancer drugs were calculated and compared to control. The results of these studies are summarized in FIGS. 14 to 20. As these results show, HSPI (Sequence ID No. 1) by itself acts as a cytotoxin for stomach cancer cells. However, HSPI (Sequence ID No. 1) used in combination with the various anticancer drugs gives rise to a significantly enhanced cytoxic effect on cancerous cells as illustrated in FIGS. 14-20. The symbiotic effect obtained with the various combinations is evidenced by comparison to the pure HSPI (Sequence ID No. 1) and anticancer drugs. It is anticipated that there will be an increased therapeutic effect. Specifically, as a significantly increased growth inhibitory effect is obtained with the above disclosed combinations utilizing lower concentrations of the anticancer drugs compared to the treatment regimes in which the drugs are used alone, there is the potential to provide therapy wherein adverse side effects associated with the anticancer drugs are considerably reduced than normally observed with the cancer drugs used alone in larger dosages.

The applicability of HSPI, the peptide sequences (Sequence ID Nos. 2 to 4) demonstrating an efficacy for inhibiting tumour growth and combinations of HSPI (Sequence ID No. 1) and these sequences with known anticancer drugs for the treatment of various cancers found in mammals such as prostate cancer, breast and gastrointestinal cancer will be readily apparent to those skilled in the art. Further, the use of HSPI (Sequence ID No. 1) and suitable fragments thereof for treatment of benign prostate hyperplasia will also be apparent to those skilled in the art. The studies disclosed herein are interpreted to mean that HSPI (Sequence ID No. 1), the shorter peptides (Sequence ID Nos. 2 to 4) and combinations thereof with various cancer drugs will exhibit an efficacy in the treatment of diseases characterized by elevated levels of FSH in the body.

Various amounts of HSPI (Sequence ID No.1) in the range of 10-50 $\mu$g have been administered to adult male rats for a period of 4 to 12 weeks with no adverse toxic effect on body weight, or in parameters measured by clinical chemistry.

Those skilled in the art will be aware of pharmaceutically appropriate dosage forms for the mixtures of HSPI (Sequence ID No. 1) and the anticancer as well as the manner in which a suitable dosage quantity and regimen may be derived in respect of a particular patient suffering from cancer of the gastrointestinal tract. In addition, those skilled in the art will also appreciate that such dosages may be encapsulated in time release delivery systems comprising for example a liposome delivery system, polysaccharides exhibiting a slow release mechanism, salistic or other polymer implants or microspheres.

While HSPI (Sequence ID No. 1) and the peptide analogues (Sequence ID Nos. 2 to 4) associated therewith, and combinations of HSPI and these peptide analogues with anticancer drugs has been disclosed herein as exhibiting an efficacy for the treatment of prostate cancer and cancer of the gastrointestinal tract, it will be appreciated by those skilled in the art that numerous variations exist with respect to therapeutically treating various cancers characterized by elevated FSH levels HSPI (Sequence ID No. 1) the peptide analogues (Sequence ID Nos. 2 to 4) and combinations of these compounds with various anticancer drugs without departing from the scope of the invention.

TABLE I

EFFECT OF HSPI ADMINISTRATION ON THE SERUM LEVELS OF FSH AND LH ($\mu$G ml$^{-1}$) IN INTACT ADULT MALE RATS

| | FSH | | | | LH | | | |
|---|---|---|---|---|---|---|---|---|
| | Saline | 100 ng | 1 $\mu$g | 10 $\mu$g | Saline | 100 ng | 1 $\mu$g | 10 $\mu$g |
| mean | 349 | 267.4* | 223.7* | 132* | 402.2 | 398 | 386 | 351 |
| ±SEM (n = 5) | ±20.8 | ±10.9 | ±10.2 | ±12.1 | ±28.6 | ±15.6 | ±30.3 | ±21.2 |
| % supp. | — | 19.4 | 32.6 | 60.2 | — | 2.4 | 5.1 | 11.5 |

*$P < 0.001$, in comparison with saline control. HSPI was administered (s.c.) daily for 3 days, and blood collected 2 h after the last injection.

TABLE II

EFFECT OF HSPI ON CELL PROLIFERATION

| TREATMENT | | CELL COUNT | |
|---|---|---|---|
| | 3 DAYS | | 7 DAYS |
| CELLS/ WELL | INHIBI- TION % | CELLS/ WELL | INHIBI- TION |
| CONTROL | 2150 | 0 | 1.44 × 10$^4$ | 0 |
| 10/$\mu$g | 330 | 84 | 0.28 × 10$^4$ | 80 |
| 5/$\mu$g | 1165 | 45 | 0.708 × 10$^4$ | 50 |
| 1/$\mu$g | 2000 | 7 | 0.958 × 10$^4$ | 30 |

R-3327 (G) cells were seeded at a cell density 500 cells/well in 16 mm multiwell plates in MEM supplemented with 15% FBS. Different concentrations of HSPI were added as indicated. One plate was counted on day 3 while the other plate was supplemented with indicated amount of HSPI and cell counts were carried out 7 days after initial addition of HSPI. Percentage inhibition was calculated taking control as 100%. Values are means of triplicate.

TABLE III

EFFECT OF HSPI ON WEIGHT OF TESTIS AND PROSTATE WEIGHT (GRAMS)

| | TESTIS | PROSTATE |
|---|---|---|
| SALINE CONTROL | 3.26 ± 0.19 | 1.26 ± 0.24 |
| HSPI TREATED | 3.56 ± 0.31 | 1.11 ± 0.21 |

TABLE IV

| GROUPS HSPI DOSAGE | % VIABILITY WHEN COMPARED TO CONTROLS |
|---|---|
| 0-CONTROL | 100% |
| 5 picograms | 100% |
| 50 picograms | 100% |
| 0.50 nanograms | 85% |
| | (mean from two expts.) |
| 5 nanograms | 68% |
| 50 nanograms | 63% |
| 500 nanograms | 64% |
| | (mean from two expts.) |
| 5 micrograms | 70% |

TABLE V

HORMONE LEVELS IN THE RATE CIRCULATION ANIMALS TREATED DAYS 3-13. ANIMALS SACRIFICED ON DAY 14.

| DOSE | % TUMOUR INHIBITION | FSH (NG/ML) | PROLACTIN (NG/ML) | LH (NG/ML) | TESTO. (NG/ML) | PIP (NG/ML) |
|---|---|---|---|---|---|---|
| CONT. | 0 | 9.35 ± .92 | 415 ± 194 | .68 ± .24 | 1.4 ± .27 | 7.48 ± 0.5 |
| 5 NG | 32% | 4.6 ± .95 | 273 ± 93 | .39 ± .03 | 2.0 ± .67 | 7.0 ± 1.3 |
| 50 NG PIP | 39% | 3.73 ± .36 | 245 ± 70 | .30 ± .04 | 1.1 ± .98 | 9.39 ± 1.0 |

---

Therefore what is claimed is:

1. A method of inhibiting the growth of adenocarcinoma of the prostate comprising administering human seminal prostatic inhibin (Sequence ID No. 1) to the prostate in a dosage range from about 500 picograms/kg/day to about 1 milligrams/kg/day.

2. The method according to claim 1 wherein the human seminal prostatic inhibin is administered in a dosage range from about 5 nanograms/kg/day to about 10 micrograms/kg/day.

3. The method according to claim 1 wherein the human seminal prostatic inhibin is administered in a mixture comprising the human seminal prostatic inhibin (Sequence ID No. 1) and a pharmaceutically acceptable carrier.

4. The method according to claim 3 wherein the human seminal prostatic inhibin is administered in a dosage range from about 5 nanograms/kg/day to about 500 nanograms/kg/day.

5. The method according to claim 1 wherein said human prostatic inhibin is administered in a mixture including an anticancer drug selected from the group consisting of mitomycin, idarubicin, cisplatin, 5-fluoro-uracil, methotrexate, adriamycin and daunomycin, wherein the anticancer drug is present in the mix in the range from about 0.1 to 9 micrograms per 1 microgram of said human prostatic inhibin.

6. A method of inhibiting the growth of adenocarcinoma of the prostate comprising administering decapeptide (Sequence ID No. 2) to the prostate in a dosage range from about 250 nanograms/kg/day to about 1 milligrams/kg/day.

7. A composition for inhibiting adenocarcinoma of the prostate, comprising:
  a) human seminal prostate inhibin (Sequence ID No. 1) present in a dosage range of about 5 nanograms/kg/day to about 10 micrograms/kg/day; and
  b) an anticancer drug.

8. A composition according to claim 7 wherein said anticancer drug is selected from the group consisting of mitomycin, idarubicin, cisplatin, 5-fluoro-uracil, methotrexate, adriamycin and daunomycin.

9. A composition according to claim 7 including a pharmaceutically acceptable carrier.

10. A composition according to claim 9 wherein the pharmaceutically acceptable carrier includes time release encapsulationmeans for effecting continual dosing of the composition.

* * * * *